United States Patent
Fukushima et al.

(10) Patent No.: US 7,842,431 B2
(45) Date of Patent: Nov. 30, 2010

(54) MIXTURE, CATION CONDUCTOR AND ELECTROCHEMICAL DEVICE USING THOSE

(75) Inventors: Kazuaki Fukushima, Kanagawa (JP); Takuro Hirakimoto, Kanagawa (JP); Shuichi Takizawa, Kanagawa (JP); Atsushi Nishimoto, Kanagawa (JP); Kazuhiro Noda, Kanagawa (JP)

(73) Assignee: Sony Corporation, Tokyo (JP)

( * ) Notice: Subject to any disclaimer, the term of this patent is extended or adjusted under 35 U.S.C. 154(b) by 681 days.

(21) Appl. No.: 11/463,228

(22) PCT Filed: Feb. 2, 2005

(86) PCT No.: PCT/JP2005/001473

§ 371 (c)(1),
(2), (4) Date: Aug. 8, 2006

(87) PCT Pub. No.: WO2005/078741

PCT Pub. Date: Aug. 25, 2005

(65) Prior Publication Data

US 2007/0111073 A1 May 17, 2007

(30) Foreign Application Priority Data

Feb. 16, 2004 (JP) .............................. 2004-38683

(51) Int. Cl.
*H01M 8/10* (2006.01)
*H01M 10/0564* (2006.01)
(52) U.S. Cl. .................. 429/491; 429/307; 429/314
(58) Field of Classification Search .................. 429/33, 429/307, 314; 252/62.2
See application file for complete search history.

(56) References Cited

U.S. PATENT DOCUMENTS

| | | | | |
|---|---|---|---|---|
| 6,120,696 | A * | 9/2000 | Armand et al. | 252/62.2 |
| 6,171,522 | B1 | 1/2001 | Michot et al. | |
| 6,264,857 | B1 * | 7/2001 | Kreuer et al. | 429/33 X |
| 7,135,537 | B2 * | 11/2006 | Hofmann | 429/33 X |
| 7,285,616 | B2 * | 10/2007 | Yoshimura et al. | 429/33 X |
| 2004/0146766 | A1 * | 7/2004 | Li et al. | 429/30 |

FOREIGN PATENT DOCUMENTS

JP 2000-508114 A 6/2000

(Continued)

OTHER PUBLICATIONS

Noda et al., "Bronsted Acid—Base Ionic Liquids as Proton-Conducting Nonaqueous Electrolytes," The Journal of Physical Chemistry B., vol. 107, No. 17, May 2003, pp. 4024-4033.

(Continued)

*Primary Examiner*—Stephen J. Kalafut
(74) *Attorney, Agent, or Firm*—K&L Gates LLP

(57) ABSTRACT

A mixture, cation conductor and electrochemical device using same are provided. The mixture and a cation conductor, in which cations can be moved without humidification even in a range of temperatures less than or equal to the boiling point of water, or an electrochemical device such as a fuel cell using them. A fuel electrode and an oxygen electrode, which are oppositely arranged with an electrolyte film in between, is provided. The electrolyte film contains a first compound formed of an imidazole derivative containing N having an unshared electron pair and a second compound of at least one selected from the group consisting of compounds having structures shown below.

16 Claims, 5 Drawing Sheets

FOREIGN PATENT DOCUMENTS

| | | |
|---|---|---|
| JP | 2000-302748 A | 10/2000 |
| JP | 2002-500678 A | 1/2002 |
| JP | 2002-260733 A | 9/2002 |
| JP | 2004-43407 A | 2/2004 |
| WO | 99/28292 | 6/1999 |

OTHER PUBLICATIONS

Masayoshi Watanabe, "Possibility of proton-conducting ionic liquids as non-humidifying and intermediate temperature fuel cell electrolytes," Abstract of Polymer Frontier 21, Sep. 16, 2003, pp. 29-34.

Kreuer et al., "Imidazole and pyrazole-based proton conducting polymers and liquids," Electrochimica Acta, 1998, vol. 43, pp. 1281-1288.

Susan et al., "Bronsted acid-based ionic liquids and their use as new materials for anhydrous proton conductors," Chem. Comun, 2003, pp. 938-939.

Sudesh et al., "Synthesis, structure and properties of polyhydroxyalkanoates: biological polyesters," Prog. Polym. Sci. 25 (2000) pp. 1503-1555.

Japanese Office Action dated Sep. 8, 2009, for corresponding Patent Application 02004-038683.

Chemical Communications, 2003, (8), p. 938-939.

Chemische Berichte, 1960, 93, p. 2410-2414.

Chemische Berichte, 1955, 88, p. 533-541.

* cited by examiner

MIXTURE, CATION CONDUCTOR AND ELECTROCHEMICAL DEVICE USING THOSE

CROSS REFERENCE TO RELATED APPLICATIONS

The present application claims priority to Japanese Patent Document No. P2004-38683 filed on Feb. 16, 2004, the disclosure of which is herein incorporated by reference.

The present invention relates to a mixture and a cation conductor, which contain compounds having specific structures, and an electrochemical device.

In recent years, a fuel cell has attracted attention as an environment-conscious electric energy generating device for the next generation, and development thereof has been actively promoted in various fields, since the fuel cell can convert fuel energy to electric energy very efficiently and the fuel cell is clean since the fuel cell does not release environmental pollutant such as nitrogen oxides.

The fuel cell can be broadly classified according to types of proton conductors. The reason thereof is that characteristics of the proton conductor largely depend on usage conditions or usage temperatures of the fuel cell. Therefore, improving the characteristics of the proton conductor is a key to obtain high-performance fuel cells.

Of these fuel cells, there is a fuel cell using a proton conductive membrane as a proton conductor. As a representative polymer membrane, a polyperfluorosulfonic acid membrane or its improved products and the like are known. In addition, a hydrocarbon membrane has been reported.

When these proton conductive membranes are in the wet state, these membranes show high proton conductivity at temperatures in the vicinity of ambient temperatures. For example, the proton conductive membrane using the polyperfluorosulfonic acid contains a large amount of water in the film. Protons released from a sulfonic acid group move through the water as a channel, and thereby the proton conductivity emerges. Therefore, in order to maintain this proton conductivity at a high level, it is necessary to continuously resupply water in using the fuel cell to maintain the proton conductive membrane in the wet state.

However, in the fuel cell using such a proton conductive membrane, a humidifier for resupplying water to gas supplied to the battery, or a peripheral for controlling moisture in the proton conductive membrane is required, which leads to a complicated and large system as a whole. Therefore, it has been a disadvantage that facility costs or operation costs become high. Further, there has been a disadvantage that it is not usable in the region at equal to or higher than boiling point of water.

Therefore, a nonaqueous proton conductor, in which a polymer doped with phosphoric acid or imidazole and protonic acid are mixed has been suggested (for example, refer to M. Rikukawa et al., "Progress polymer science," 2000, 25, pp. 1463-1502; K, D. Kreuer et al., "Electrochimica Acta," 1988, 43, pp. 1281-1288; M. A. B. H. Susan et al., "Chemical Communications," 2003, pp. 938-939; and Noda, A. et al., "Journal of physical chemistry B," 2003, 107, pp. 4024-4033). In these proton conductors, it is considered that protons are conducted not through water, but though self-dissociation phosphoric acid or a nitrogen site of imidazole.

However, in these proton conductors, phosphoric acid and imidazole are easily dissolved in water. Therefore, there has been a shortcoming that when the fuel cell is operated at room temperatures, the proton conductor is gradually eluted from inside due to water generated in an oxygen electrode in generating power, and a degree of proton conductivity is decreased. Therefore, when these proton conductors are used, though it is usable at equal to or higher than boiling point of water, long-term continuous use has been difficult at the boiling point or less of water.

SUMMARY

In view of foregoing, it is an object of the invention to provide a mixture and a cation conductor capable of conducting cations without humidification even in a range of temperatures equal to or less than the boiling point of water, and an electrochemical device such as a fuel cell using the mixture or the cation conductor.

The mixture according to the invention contains: a first compound formed of an imidazole derivative containing nitrogen (N) having an unshared electron pair; and a second compound of at least one selected from the group consisting of a compound having a structure expressed in Chemical formula 1, a compound having a structure expressed in Chemical formula 2, and a compound having a structure expressed in Chemical formula 3.

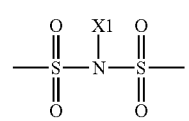

Chemical formula 1

In Chemical formula 1, X1 represents an element of Group 1 in the long-period periodic table.

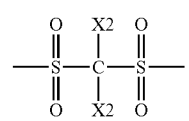

Chemical formula 2

In Chemical formula 2, X2 represents an element of Group 1 in the long-period periodic table.

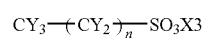

Chemical formula 3

In Chemical formula 3, Y represents hydrogen or halogen, and X3 represents an element of Group 1 in the long-period periodic table. n represents a positive integer.

The cation conductor of the invention contains a first compound formed of an imidazole derivative containing nitrogen having an unshared electron pair; and a second compound of at least one selected from the group consisting of a compound having a structure expressed in Chemical formula 4, a compound having a structure expressed in Chemical formula 5, and a compound having a structure expressed in Chemical formula 6.

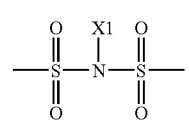

Chemical formula 4

In Chemical formula 4, X1 represents an element of Group 1 in the long-period periodic table.

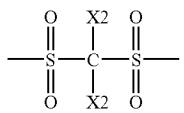

Chemical formula 5

In Chemical formula 5, X2 represents an element of Group 1 in the long-period periodic table.

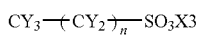

Chemical formula 6

In Chemical formula 6, Y represents hydrogen or halogen, and X3 represents an element of Group 1 in the long-period periodic table. n represents a positive integer.

The electrochemical device of the invention is an electrochemical device, wherein a pair of electrodes is arranged with a cation conductor in between, wherein the cation conductor contains: a first compound formed of an imidazole derivative containing nitrogen having an unshared electron pair; and a second compound of at least one selected from the group consisting of a compound having a structure expressed in Chemical formula 7, a compound having a structure expressed in Chemical formula 8, and a compound having a structure expressed in Chemical formula 9.

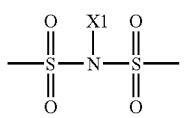

Chemical formula 7

In Chemical formula 7, X1 represents an element of Group 1 in the long-period periodic table.

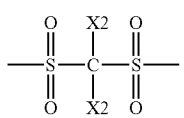

Chemical formula 8

In Chemical formula 8, X2 represents an element of Group 1 in the long-period periodic table.

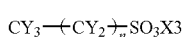

Chemical formula 9

In Chemical formula 9, Y represents hydrogen or halogen, and X3 represents an element of Group 1 in the long-period periodic table. n represents a positive integer.

According to the mixture or the cation conductor of the invention, the mixture or the cation conductor contains the first compound formed of the imidazole derivative containing nitrogen having an unshared electron pair; and the second compound of at least one selected from the group consisting of the compound having the structure expressed in Chemical formulas 1 or 4, the compound having the structure expressed in Chemical formulas 2 or 5, and the compound having the structure expressed in Chemical formulas 3 or 6. Therefore, the unshared electron pair of nitrogen contained in the first compound can accept cations of the element of Group 1 in the long-period periodic table contained in the second compound, and water solubility can be decreased. Therefore, when water does not exist, cations can be moved; and when water exists, the mixture or the cation conductor is prevented from being dissolved in water and leading to lowering cation conductivity. Consequently, according to the electrochemical device of the invention, a periphery for controlling moisture becomes unnecessary, a whole system can be miniaturized, the electrochemical device can be used at room temperatures or 100° C. or more, and the electrochemical device can be used in a broad range.

Additional features and advantages of the present invention are described in, and will be apparent from, the following Detailed Description and the Figures.

DETAILED DESCRIPTION

Figure 1:
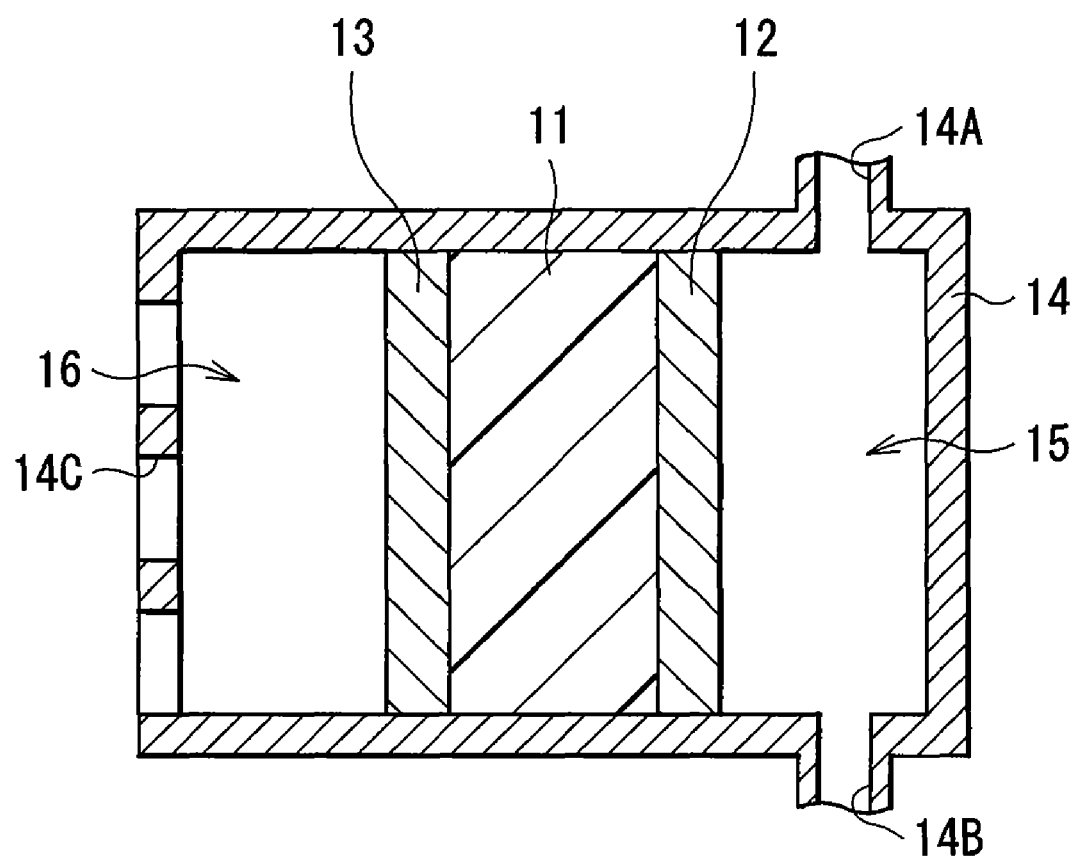
FIG. 1 is a cross section showing a structure of a fuel cell according to an embodiment of the invention.

An embodiment of the invention will be hereinafter described in detail.

A mixture according to the embodiment of the invention contains, for example, a first compound formed of an imidazole derivative containing nitrogen having an unshared electron pair; and a second compound of at least one selected from the group consisting of a compound having a structure expressed in Chemical formula 10, a compound having a structure expressed in Chemical formula 11, and a compound having a structure expressed in Chemical formula 12. An element of Group 1 in the long-period periodic table is hydrogen or an alkali metal.

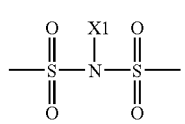

Chemical formula 10

In Chemical formula 10, X1 represents an element of Group 1 in the long-period periodic table.

Chemical formula 11

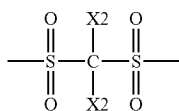

In Chemical formula 11, X2 represents an element of Group 1 in the long-period periodic table.

Chemical formula 12

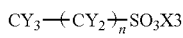

In Chemical formula 12, Y represents hydrogen or halogen, and X3 represents an element of Group 1 in the long-period periodic table. n represents a positive integer, and is preferably 7 or more.

The first compound, that is, the imidazole derivative functions as a cation receptor. The second compound functions as a cation donor. In the invention, protons are included in cations. Since this mixture contains the first compound and the second compound as above, the mixture is difficult to dissolve in water, and at least part thereof is insoluble.

As an imidazole derivative having an unshared electron pair, for example, a compound having a substituent in at least one of the first, the second, the fourth, and the fifth positions of imidazole as expressed in Chemical formula 13; a compound in which the fourth and the fifth positions of imidazole are cyclized as expressed in Chemical formula 14; a compound in which the first and the second positions of imidazole are cyclized as expressed in Chemical formula 15; and a compound in which the first and the fifth positions of imidazole are cyclized as expressed in Chemical formula 16 can be cited. However, in the invention, benzoimidazole is not included in the imidazole derivatives. In these imidazole derivatives, nitrogen in the third has an unshared electron pair, which becomes a cation receptor part.

Chemical formula 13

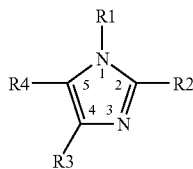

In Chemical formula 13, R1, R2, R3, and R4 represent a hydrogen group or a substituent. R1, R2, R3, and R4 can be identical with or different from each other. However, it is necessary that at least one thereof is a substituent.

Chemical formula 14

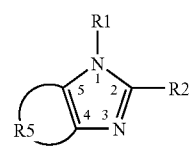

In Chemical formula 14, R1 and R2 represent a hydrogen group or a substituent. R1 and R2 can be identical with or different from each other. R5 represents a group containing carbon.

Chemical formula 15

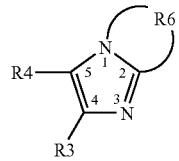

In Chemical formula 15, R3 and R4 represent a hydrogen group or a substituent. R3 and R4 can be identical with or different from each other. R6 represents a group containing carbon.

Chemical formula 16

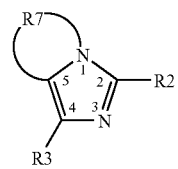

In Chemical formula 16, R2 and R3 represent a hydrogen group or a substituent. R2 and R3 can be identical with or different from each other. R7 represents a group containing carbon.

Here, substituents of R1 to R4 can be a substituent having carbon or a halogen group, but is preferably the substituent having carbon.

In the substituent having carbon, the number of carbon is preferably 1 to 20. When the number of carbon is larger than 20, movability of cations is decreased.

Further, the substituent having carbon can contain hetero atoms such as nitrogen, oxygen (O), phosphorous (P) and sulfur (S).

Further, as a substituent having carbon, for example, an alkyl group, an aryl group, and a group in which at least one hydrogen of the alkyl group or the aryl group is substituted with halogen can be cited. Specially, a phenyl group, a benzyl group, an alkyl group whose number of carbon is 1 to 4, or a group in which at least one hydrogen of the phenyl group, the benzyl group, or the alkyl group whose number of carbon is 1 to 4 is substituted with halogen is preferable. The reason thereof is that the imidazole derivative itself becomes difficult to dissolve in water, and solubility of the mixture is decreased.

The more the imidazole derivative having an unshared electron pair is substituted, the lower its water solubility is. However, it is preferable that R1 is hydrogen since movability of cations can be improved.

For example, as such an imidazole derivative, an imidazole derivative in which a substituent is bonded to the second position and hydrogen is bonded to first, fourth and fifth positions, such as 2-i-propylimidazole expressed in Chemical formula 17, 2-ethylimidazole expressed in Chemical formula 18, 2-n-propylimidazole expressed in Chemical formula 19, 2-butylimidazole expressed in Chemical formula 20 and 2-phenylimidazole expressed in Chemical formula 21, can be preferably cited.

Chemical formula 17

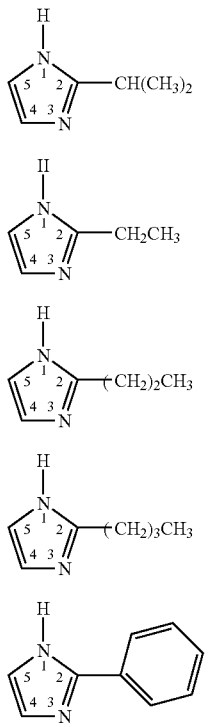

Chemical formula 18

Chemical formula 19

Chemical formula 20

Chemical formula 21

Further, an imidazole derivative in which a hydrogen group is bonded to the first position, a substituent is bonded to the second position, and a substituent is bonded to at least one of the fourth and fifth positions, such as 2-ethyl-4-methyl-imidazole expressed in Chemical formula 22 can be preferable cited.

Chemical formula 22

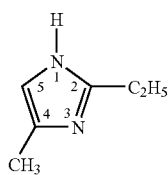

Of the second compound, the compound having the structure expressed in Chemical formula 10 or Chemical formula 11 can be a polymer containing such a structure. As a compound having the structure expressed in Chemical formula 10, for example, a compound expressed in Chemical formula 23 can be cited.

Chemical formula 23

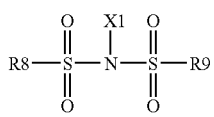

In Chemical formula 23, R8 and R9 represent an alkyl group, a phenyl group, or a derivative thereof. R8 and R9 can be identical with or different from each other. X1 represents an element of Group 1 in the long-period periodic table.

Concrete examples of the compound expressed in Chemical formula 23 include compounds expressed in Chemical formulas 24 to 27.

Chemical formula 24

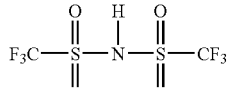

Chemical formula 25

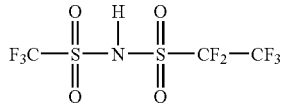

Chemical formula 25

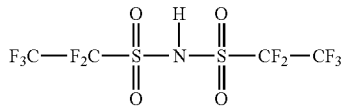

Chemical formula 27

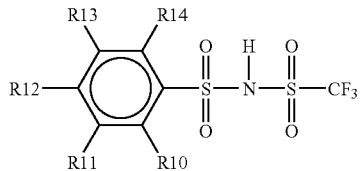

In Chemical formula 27, R10 to R14 represent a hydrogen group, a fluorine group, a methyl group, a methyl fluoride group, or a methoxyl group. R10 to R14 can be identical with or different from each other.

The mixture is used as a cation conductor, for example.

In this case, when cation conductivity is shown by only the first compound and the second compound, the mixture can be used as a cation conductor as it is. However, it is possible to use the mixture by dissolving the mixture in a solvent according to needs. As a solvent, for example, cyclic or chain carbonic acid ester such as ethylene carbonate, propylene carbonate, butylene carbonate, dimethyl carbonate, ethyl methyl carbonate, and diethyl carbonate, and alkyl ether fluoride can be cited.

Further, the foregoing mixture can be supported by a support. The support preferably supports and forms the mixture in a state of a film or the like. The support can be an organic matter, an inorganic matter, or a complex thereof. As an inorganic material forming the support, silicon dioxide (silica) or a derivative thereof, or a polymer thereof can be cited. Further, as an organic polymer forming the support, for example, a fluorinated polymer such as poly (vinylidene fluoride), a copolymer of vinylidene fluoride and hexafluoro propylene, and polytetrafluoroethylene; a heat-resistant high molecule such as polyimide, polyamide, polybenzimidazole, and polyphenylene oxide; an ether compound such as poly (ethylene oxide); poly (acrylonitrile); and a cross-linked compound having a functional group such as a methacrylate group and an acrylate group can be cited. As a form of the support, a porous film of these polymers such as a porous film of polyimide can be cited.

When the foregoing mixture is liquid, the mixture is directly supported by the polymer. When the foregoing mixture is solid, the mixture is dissolved in a solvent to obtain a liquid mixture, which is supported by the polymer. In these cases, the resultant becomes so-called gelatinous.

This cation conductor can be formed as follows, for example.

First, the first compound formed of the imidazole derivative having an unshared electron pair; and the second compound of at least one selected from the group consisting of the compound having the structure expressed in Chemical formula 10, the compound having the structure expressed in Chemical formula 11, and the compound having the structure expressed in Chemical formula 12 are mixed under the argon (Ar) atmosphere at, for example, a moisture concentration of 10 ppm or less to form a mixture. In this atmosphere, the first compound and the second compound can be mixed uniformly. This mixture becomes liquid or solid at room temperatures according to mixture ratios between the first compound and the second compound.

Next, the obtained mixture can be dissolved in a solvent according to needs. Further, it is possible that the mixture or the mixture dissolved in the solvent is supported by a support to obtain a film. For example, when a polymer is used as a support, it is possible that the mixture, the polymer, and the solvent according to needs are mixed by using a mixed solvent to obtain a film, and then the mixed solvent is volatilized. Otherwise, it is possible that after a proton conductive membrane or a porous film is formed, the mixture or the mixture dissolved in the solvent is impregnated or absorbed into such a film. Further, it is possible that the mixture, a monomer organizing the high molecule compound, and the solvent according to needs are mixed to obtain a film, and then the monomer is polymerized or cross-linked. In this case, a polymerization initiator or a cross-linking agent is added according to needs. Further, in mixing, it is possible that after or before the mixed solvent is added and polymerization is performed, the mixed solvent is volatilized.

According to the mixture or the cation conductor according to the embodiment, the first compound formed of the imidazole derivative including nitrogen having an unshared electron pair; and the second compound of at least one selected from the group consisting of the compound having the structure expressed in Chemical formula 10, the compound having the structure expressed in Chemical formula 11, and the compound having the structure expressed in Chemical formula 12 are contained. Therefore, the unshared electron pair of nitrogen contained in the first compound can accept cations of the element of Group 1 in the long-period periodic table contained in the second compound. Therefore, cations can be moved without water, and water solubility can be decreased. Therefore, when water exists, it is possible to prevent the mixture or the cation conductor from being dissolved in water leading to decrease in cation conductivity.

Next, a fuel cell using this cation conductor will be described.

FIG. 1 shows a structure of the fuel cell according to the embodiment of the invention. The fuel cell has a fuel electrode 12 and an oxygen electrode 13, which are oppositely arranged with an electrolyte film 11 in between. The electrolyte film 11, the fuel electrode 12, and the oxygen electrode 13 are contained in an exterior member 14. In the exterior member 14, a fuel chamber 15 is provided adjacently to the fuel electrode 12, and an oxygen chamber 16 is provided adjacently to the oxygen electrode 13. The fuel chamber 15 is connected with a not-shown fuel supply part through distribution holes 14A and 14B provided in the exterior member 14. Liquid fuel containing hydrogen, methanol, ethanol, dimethyl ether or the like is supplied from the fuel supply part. The oxygen chamber 16 is connected with outside through a distribution hole 14C provided in the exterior member 14. Air, that is, oxygen is supplied to the oxygen electrode 13 by natural ventilation.

The electrolyte film 11 is, for example, formed of the foregoing cation conductor film. In this case, protons are conducted in the fuel cell. Therefore, X1 of Chemical formula 10, X2 of Chemical formula 11, and X3 of Chemical formula 12 in the second compound are formed of hydrogen. The electrolyte film 11 is formed of an electrolyte film or a proton conductor.

The fuel electrode 12 and the oxygen electrode 13 have, for example, a structure in which a catalyst layer containing a catalyst such as platinum (Pt) and ruthenium (Ru) is formed on a gas diffusion layer made of a carbon paper or the like. The catalyst layer is made of, for example, a substance in which a carrier such as carbon black supporting the catalyst is dispersed in a proton conduction material.

This fuel cell can be formed as follows, for example.

The fuel electrode 12 and the oxygen electrode 13 are layered with the electrolyte film 11 made of the foregoing proton conductor in between. The fuel electrode 12 and the oxygen electrode 13 are bonded by, for example, thermocompression bonding. A temperature and a pressure for the thermocompression bonding are preferably, for example, 100° C. to 150° C. and 20 kgf/cm$^2$ to 40 kgf/cm$^2$. When the temperature is too low or the pressure is too low, bonding between the electrolyte film 11 and the fuel electrode 12 or the oxygen electrode 13 becomes insufficient. When the temperature is too high, the proton conductor contained in the electrolyte film 11 may be decomposed. When the pressure is too high, the current collector of the fuel electrode 12 and the oxygen electrode 13 may be damaged. Time for the thermocompression bonding is preferably, for example, 30 sec to 5 min. When the time is shorter than 30 sec, bonding between the electrolyte film 11 and the fuel electrode 12 or the oxygen electrode 13 becomes insufficient. When the time is longer than 5 min, the proton conductor contained in the electrolyte film 11 may be decomposed.

Subsequently, the obtained electrolyte film 11, the obtained fuel electrode 12, and the obtained oxygen electrode 13 are contained in the exterior member 14. Thereby, the fuel cell shown in FIG. 1 is completed.

In this fuel cell, fuel is supplied to the fuel electrode 12, and protons and electrons are generated by reaction. Protons move to the oxygen electrode 13 via the electrolyte film 11, and reacts with electrons and oxygen to generate water. Then, in the electrolyte film 11, protons are conducted by using nitrogen having an unshared electron pair contained in the imidazole derivative, which is the first compound as a proton receptor. Therefore, even when water does not exist, proton conductivity can be obtained. Further, since the electrolyte film 11 contains the first compound and the second compound, water solubility is low. Therefore, even when water exists, the electrolyte film 11 is prevented from being dissolved in water to decrease proton conductivity.

As above, according to the fuel cell according to the embodiment, the proton conductor according to the embodiment is used. Therefore, it is possible to start the fuel cell at low yield temperatures in short time. In addition, a periphery for controlling moisture is unnecessary. Therefore, the whole system can be miniaturized. Further, the fuel cell can be used at room temperatures or 100° C. or more, that is, can be used in the broad temperature range.

EXAMPLES

Further, concrete examples of the invention will be described in detail.

Examples 1-1 to 1-6

The mixture described in the embodiment was formed. As the first compound, 2-phenylimidazole (hereinafter referred to as "2PhIm") expressed in Chemical formula 21 was used. As the second compound, pentafluoroethanesulfonimide (hereinafter referred to as "HBETI") expressed in Chemical formula 26 was used. In Examples 1-1 to 1-6, a mole ratio in the mixture between 2PhIm and HBETI was changed as 2PhIm:HBETI=4:6, 5:5, 6:4, 7:3, 8:2, or 9:1. Specifically, relative to 1.524 g (4.00 mmol) of HBETI, 2PhIm was mixed at a rate of 0.3842 g (2.66 mmol) in Example 1-1, 0.5763 g (4.00 mmol) in Example 1-2, 0.8644 g (6.00 mmol) in Example 1-3, 1.345 g (9.34 mmol) in Example 1-4, 2.305 g (16.0 mmol) in Example 1-5, and 5.187 g (36.0 mmol) in Example 1-6. This mixing was performed in a glove box under the argon (Ar) atmosphere at a moisture concentration of 10 ppm or less, at 150° C. equal to or higher than the melting point of 2PhIm (136° C.) for 5 min. The operation was performed three times. The mixtures obtained as above were liquid at ambient temperatures in Examples 1-1, 1-3, and 1-4, in which the mole ratios between 2PhIm and HBETI were 4:6, 6:4, and 7:3; and solid in Examples 1-2, 1-5, and 1-6, in which the mole ratios between 2PhIm and HBETI were 5:5, 8:2, and 9:1.

Figure 2:
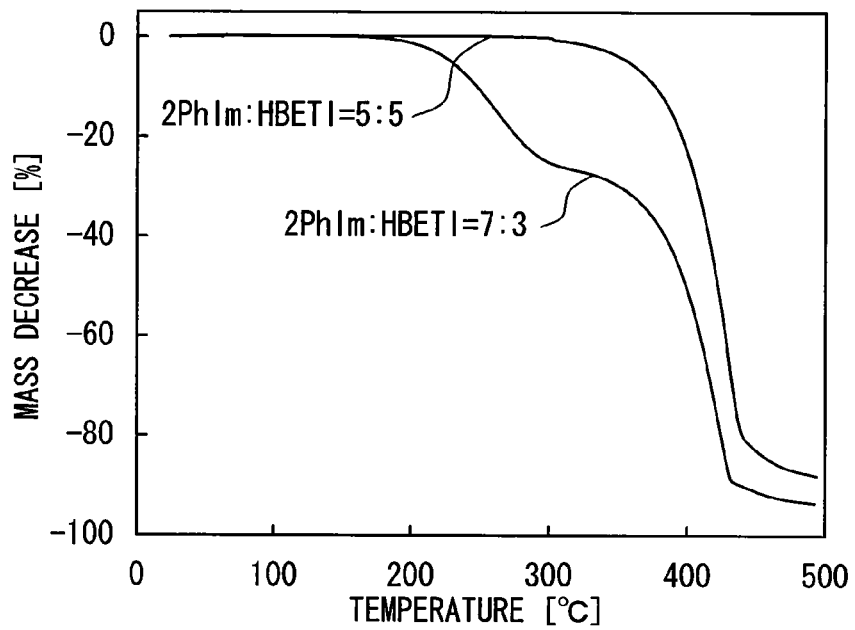
FIG. 2 is a view showing a relation between temperatures and mass decrease of mixtures formed in Example 1.

Regarding the formed mixtures, TG-DTA (thermogravimetric differential thermal analysis) was performed by setting a programming rate at 10° C./min. FIG. 2 shows Example 1-2, in which a mole ratio between 2PhIm and HBETI was 5:5 and Example 1-4, in which a mole ratio between 2PhIm and HBETI was 7:3 as representative examples of measurement results. It was found that a temperature at which a mass of the mixture of Example 1-2 was decreased by 10% was 377° C., which showed high heat resistance. Since 2PhIm was excessive in the mixture of Example 1-4, a temperature at which a mass of the mixture of Example 1-4 was decreased by 10% was 246° C. due to evaporation of 2PhIm, which was lower than in Example 1-2. However, it was found that the mass was not decreased and mixture components were not decomposed at 180° C. or less.

Further, regarding the formed mixtures, DSC (differential scanning calorimeter) measurement was performed by setting a cooling rate at 10° C./min and lowering the temperature from 100° C. to −150° C., and by setting a programming rate at 10° C./min and raising the temperature from −150° C. to 150° C. In the result, as shown in Table 1, it was found that melting points of the mixtures of Examples 1-2, 1-5, and 1-6 were decreased down to the level lower than the melting points of 2PhIm (136° C.). Further, it was found that regarding the mixtures of Examples 1-1, 1-3, and 1-4, glass transition temperatures were changed along with the mole ratios, no melting points were shown, and these mixtures became supercooled liquid.

Further, water solubility of the formed mixtures was examined. Results thereof are shown in Table 1. It was found that part of the mixture of Example 1-1 was dissolved in water and part thereof was not dissolved in water and left. It was found that the mixtures of other examples were not dissolved in water.

TABLE 1

| | First compound | Second compound | Mixing ratio | Melting point | Glass transition temperature | Water solubility |
|---|---|---|---|---|---|---|
| Example 1-1 | 2PhIm | HBETI | 4:6 | — | −40° C. | Partly dissolved |
| Example 1-2 | | | 5:5 | 53° C. | — | Not dissolved |
| Example 1-3 | | | 6:4 | — | −35° C. | Not dissolved |
| Example 1-4 | | | 7:3 | — | −30° C. | Not dissolved |
| Example 1-5 | | | 8:2 | 84° C. | — | Not dissolved |
| Example 1-6 | | | 9:1 | 106° C. | — | Not dissolved |

Figure 3:
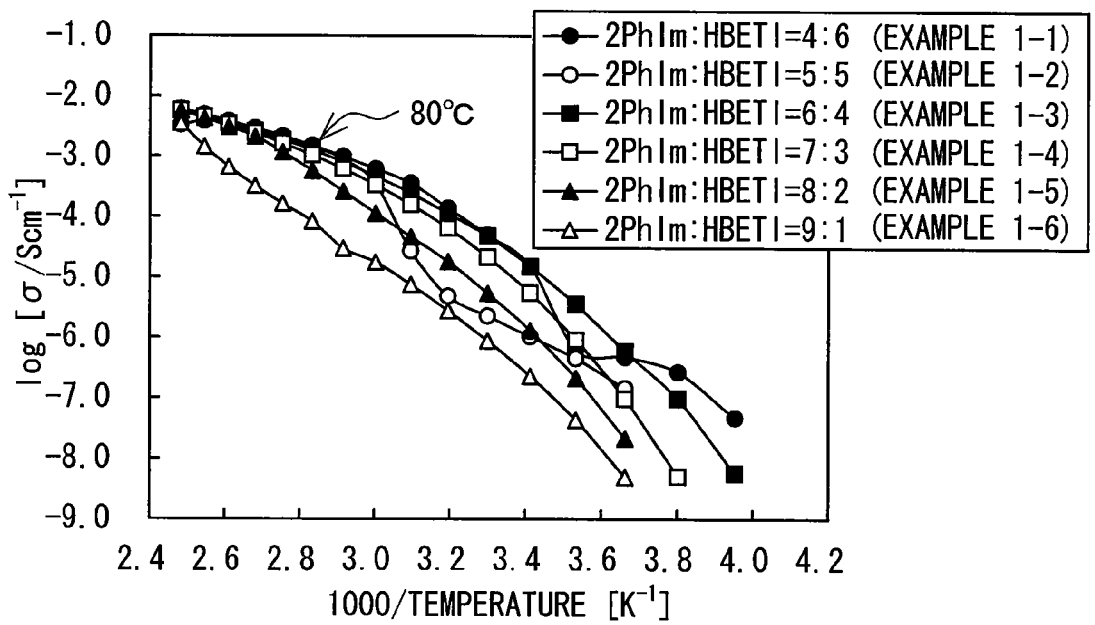
FIG. 3 is a view showing ion conductivity of mixtures formed in Example 1.

In addition, ion conductivity of the formed mixtures was measured by AC impedance measurement. FIG. 3 shows obtained results. As shown in FIG. 3, it was found that the mixtures of Examples 1-1 to 1-6 showed good ion conductivity at a temperature of 80° C. or more. In particular, it was found that the mixtures of Examples 1-1, 1-3, and 1-4 showed practical ion conductivity over $1.0 \times 10^{-3} \text{Scm}^{-1}$.

That is, it was found that in the case that a mixture contained imidazole and HBETI and did not contain an imidazole derivative, the mixture was totally dissolved in water. Meanwhile, in the case that a mixture contained 2PhIm and HBETI, the mixture was not dissolved in water, was stable at high temperatures about 200° C., and sufficient ion conductivity could be obtained.

Examples 2-1 and 2-2

Figure 4:
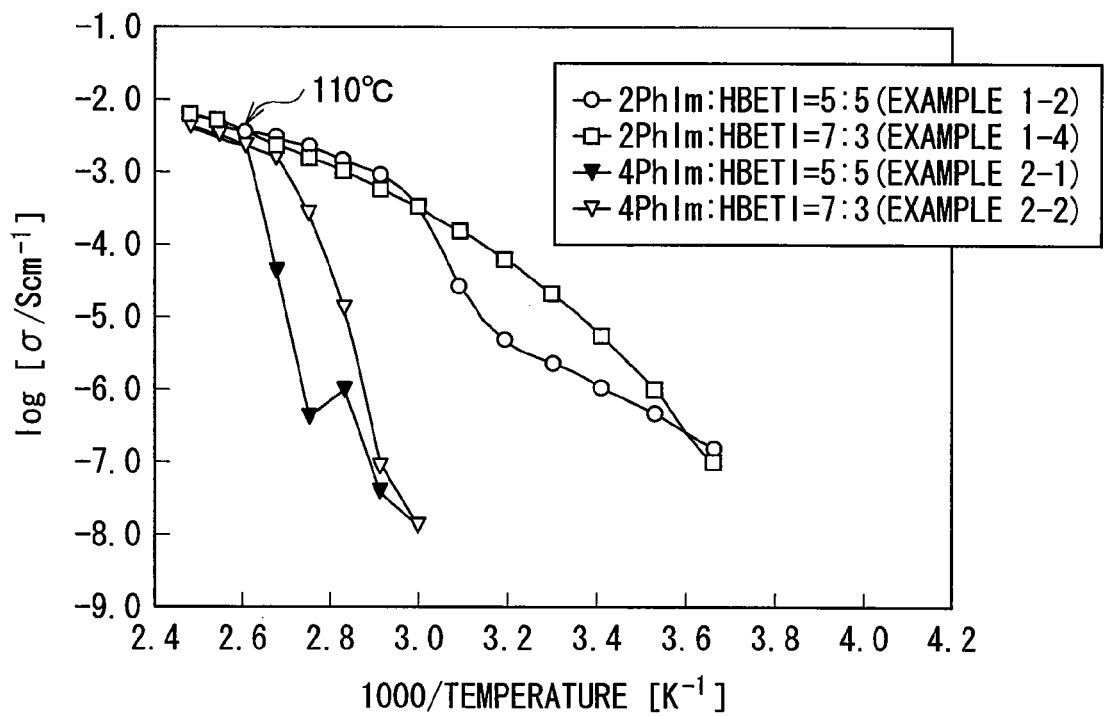
FIG. 4 is a view showing ion conductivity of mixtures formed in Example 2.

Mixtures were formed as in Examples 1-2 and 1-4, except that 4-phenylimidazole (hereinafter referred to as "4PhIm") was used as the first compound. After that, as in Examples 1-2 and 1-4, melting points and glass transition temperatures were measured by DSC measurement, and water solubility and ion conductivity by AC impedance measurement were examined. Results thereof are shown in Table 2 and FIG. 4. In FIG. 4, the results of Examples 1-2 and 1-4 are also shown.

TABLE 2

| | First compound | Second compound | Mixing ratio | Melting point | Water solubility |
|---|---|---|---|---|---|
| Example 2-1 | 4PhIm | HBETI | 5:5 | 88° C. | Not dissolved |
| Example 2-2 | | | 7:3 | 85° C. | Not dissolved |

As shown in Table 2, it was found that the melting points of the respective mixtures were decreased down to the level lower than the melting point of 4PhIm (129° C.). Further, it was found that these mixtures were not dissolved in water. Further, as shown in FIG. 4, it was found that ion conductivity equal to of Examples 1-2 and 1-4 were shown at 110° C. or more. That is, it was found that even when other imidazole was used, the mixture was not dissolved in water, and stable and sufficient ion conductivity could be obtained as in Examples 1-1 to 1-6. Further, as evidenced by comparing Examples 2-1 and 2-2 to Examples 1-2 and 1-4 in FIG. 4, Examples 1-2 and 1-4 showed ion conductivity higher than that of Examples 2-1 and 2-2 at low temperatures. The reason thereof is that the melting point is more largely decreased by mixing and system movability is more improved in the imidazole derivative having a substituent in the position of 2 than in the imidazole derivative having a substituent in the position of 4. That is, it was found that the imidazole derivative having a substituent in the position of 2 is more preferably used.

Examples 3-1-1, 3-1-2, 3-2-1, and 3-2-2

Figure 5:
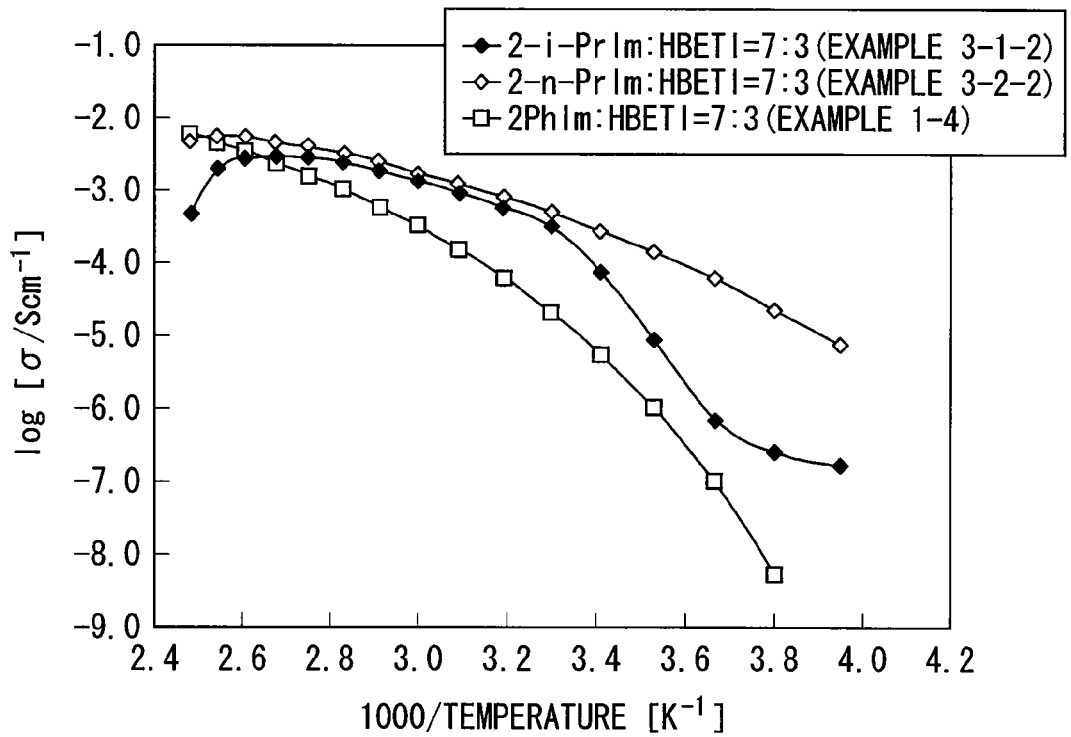
FIG. 5 is a view showing ion conductivity of mixtures formed in Example 3.

Mixtures were formed as in Examples 1-2 and 1-4, except that 2-isopropylimidazole (hereinafter referred to as "2-i-PrIm") expressed in Chemical formula 17 or 2-n-propylimidazole (hereinafter referred to as "2-n-PrIm") expressed in Chemical formula 19 was used as the first compound. After that, as in Examples 1-2 and 1-4, melting points and glass transition temperatures were measured by DSC measurement, and water solubility and ion conductivity by AC impedance measurement were examined. Results thereof are shown in Table 3 and FIG. 5. In FIG. 5, ion conductivity of mixtures of Examples 3-1-2 and 3-2-2, which were liquid at room temperatures, in which a mol ratio between 2-i-PrIm or 2-n-PrIm and HBETI was 7:3 is shown as representative examples along with the ion conductivity of Example 1-4

TABLE 3

| | First compound | Second compound | Mixing ratio | Melting point | Water solubility |
|---|---|---|---|---|---|
| Example 1-2 | 2PhIm | HBETI | 5:5 | 53° C. | Not dissolved |
| Example 1-4 | | | 7:3 | — | Not dissolved |
| Example 3-1-1 | 2-i-PrIm | | 5:5 | 50.5° C. | Partly dissolved |
| Example 3-1-2 | | | 7:3 | 15.2° C. | Partly dissolved |
| Example 3-2-1 | 2-n-PrIm | | 5:5 | 68.4° C. | Partly dissolved |
| Example 3-2-2 | | | 7:3 | — | Partly dissolved |

As evidenced by Table 3 and FIG. 5, sufficient characteristics could be obtained for all mixtures as in Examples 1-2 and 1-4. However, regarding water solubility, the order of difficulty in water solubility was as follows: Examples 1-2 and 1-4 using 2PhIm as the first compound, Examples 3-2-1 and 3-2-2 using 2-n-PrIm as the first compound, and Examples 3-1-1 and 3-1-2 using 2-i-PrIm as the first compound. Meanwhile, regarding ion conductivity, Examples 1-2 and 1-4 using 2PhIm as the first compound showed the highest degree, Examples 3-1-1 and 3-1-2 using 2-i-PrIm as the first compound showed the second highest degree, and Examples 3-2-1 and 3-2-2 using 2-n-PrIm as the first compound showed the lowest degree.

That is, the larger the number of carbon of the substituent in the first compound was, the lower water solubility could be. However, it was found that when the number of carbon was too large, ion conductivity became low.

Examples 4-1-1 and 4-1-2

Figure 6:
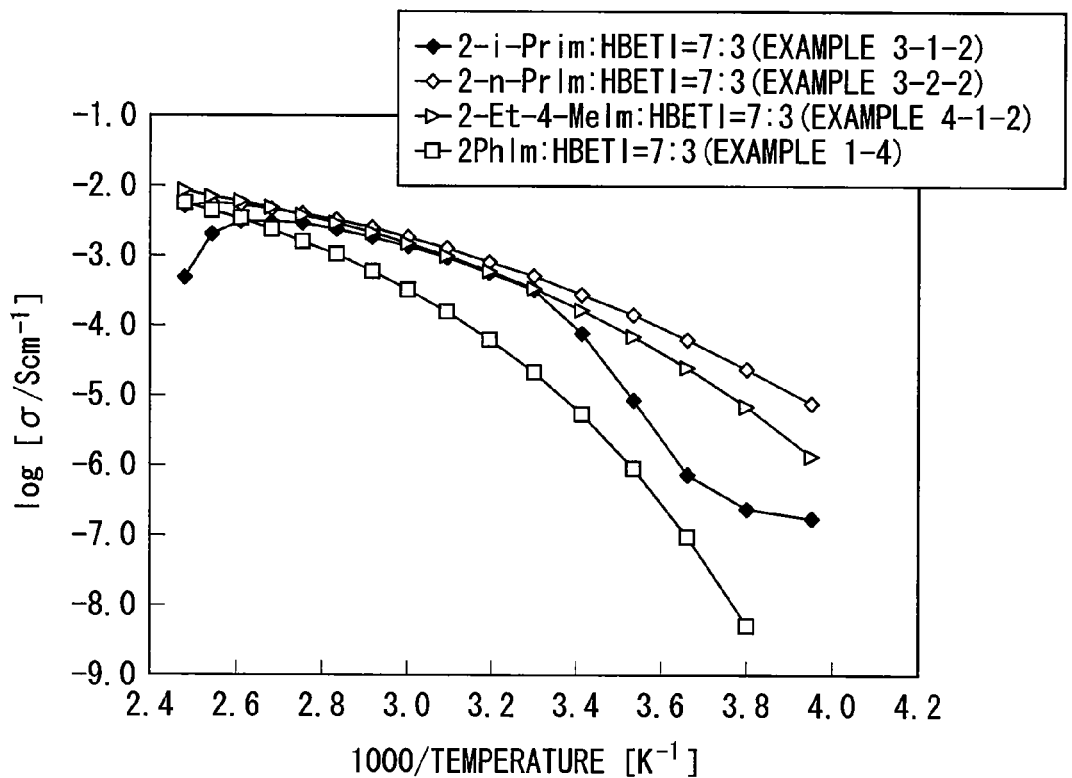
FIG. 6 is a view showing ion conductivity of a mixture formed in Example 4.

Mixtures were formed as in Examples 1-2 and 1-4, except that 2-ethyl-4-methylimidazole (hereinafter referred to as "2-Et-4-MeIm") expressed in Chemical formula 22 was used as the first compound. After that, as in Examples 1-2 and 1-4, melting points and glass transition temperatures were measured by DSC measurement, and water solubility and ion conductivity by AC impedance measurement were examined. Results thereof are shown in Table 4 and FIG. 6. In FIG. 6, ion conductivity of Example 4-1-2, which was liquid at room temperatures, in which a mol ratio between 2-Et-4-MeIm and HBETI was 7:3 is shown as a representative example along with the ion conductivity of Examples 1-4, 3-1-2, and 3-2-2.

TABLE 4

| | First compound | Second compound | Mixing ratio | Melting point | Water solubility |
|---|---|---|---|---|---|
| Example 4-1-1 | 2-Et-4-MeIm | HBETI | 5:5 | 33° C. | Partly dissolved |
| Example 4-1-2 | | | 7:3 | −14° C. | Partly dissolved |

As evidenced by Table 4 and FIG. 6, according to Examples 4-1-1 and 4-2-2, though part thereof was dissolved in water, results similar to in Examples 1-2 and 1-4 could be obtained for other characteristics. That is, it was found that when the mixture contained a compound in which hydrogen was bonded to the position of 1, a substituent was bonded to the position of 2, and a substituent was bonded to at least one of the positions of 4 and 5, the mixture was not totally dissolved and was stable even at high temperatures about 200° C., and sufficient ion conductivity could be obtained.

Example 5

Figure 7:
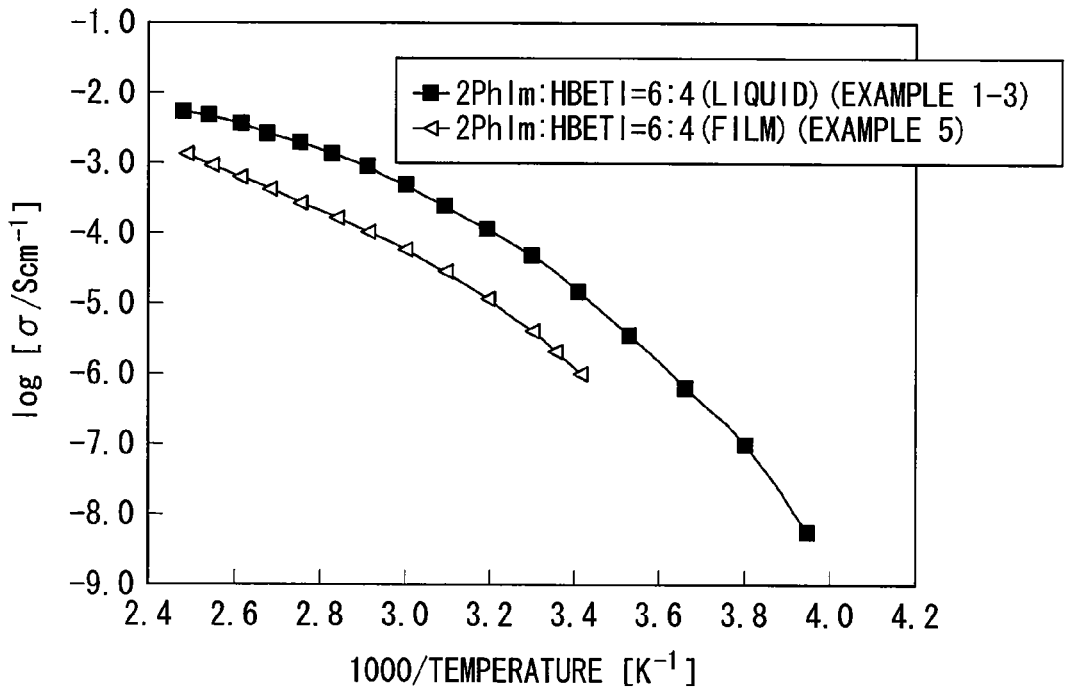
FIG. 7 is a view showing ion conductivity of a gel film formed in Example 5.

A cation conductive membrane, which was gelated by adding 20 wt % of methyl methacrylate, ethylene glycol dimethacrylate as a cross-linking agent, and azoisobutyronitrile as a radical polymerization agent to the mixture formed in Example 1-3 and performing polymerization was formed. Regarding the obtained gelated cation conductive membrane, ion conductivity was measured by AC impedance measurement as in Examples 1-1 to 1-6. An obtained result thereof is shown in FIG. 7 along with the result of Example 1-3. As evidenced by FIG. 7, according to Example 5, sufficiently high conductivity could be obtained though the value was lower than of Example 1-3. That is, it was found that even when the mixture was made into a film by adding polymers, sufficient characteristics could be obtained.

Example 6

Figure 8:
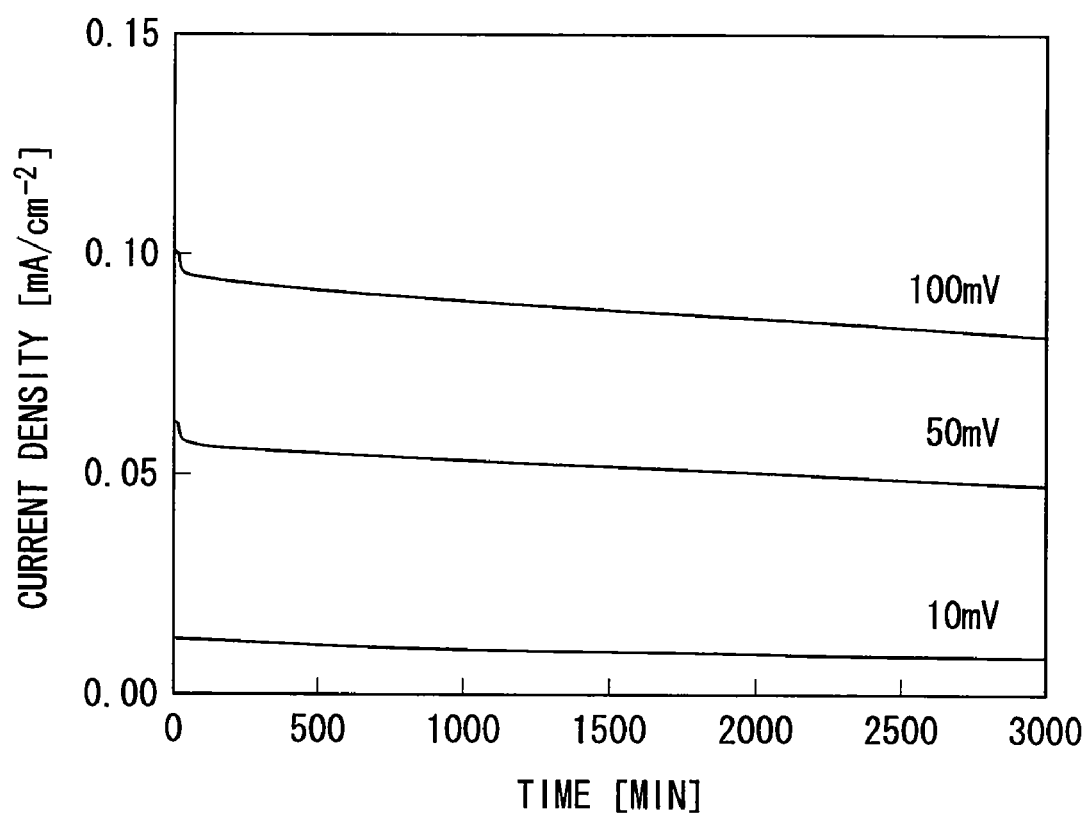
FIG. 8 is a view showing a relation between passage of time and flowing currents of a device in which a proton conductor is sandwiched between electrodes, which is formed in Example 6.

Platinum as the catalyst was supported by carbon black, with which a gas diffusion layer made of a carbon paper was coated to form a pair of electrodes. The cation conductor formed in Example 5 was sandwiched between the pair of electrodes. The resultant was applied with voltages of 10 mV, 50 mV, and 100 mV under the hydrogen atmosphere at 60° C. Results thereof are shown in FIG. 8. FIG. 8 shows a relation between passage of time and flowing currents. As evidenced by FIG. 8, currents were flowing continuously. Therefore, it could be confirmed that protons were conducted through the cation conductor.

While the invention has been described with reference to the embodiment and examples, the invention is not limited to the foregoing embodiment and examples, and various modifications may be made. For example, in the foregoing embodiment, structures of the electrolyte film 11, the fuel electrode 12, and the oxygen electrode 13 have been specifically described. However, the electrolyte film 11, the fuel electrode 12, and the oxygen electrode 13 can have other structure, or can be made of other materials.

Further, in the foregoing embodiment, fuel is supplied from the not-shown fuel supply part to the fuel electrode 12. However, it is possible that the fuel chamber is hermetically closed, and fuel is supplied according to needs.

Further, in the foregoing embodiment, air supply to the oxygen electrode 13 is performed by natural ventilation.

However, it is possible to supply air forcibly by utilizing a pump or the like. In this case, instead of air, oxygen or gas containing oxygen can be supplied.

In addition, in the foregoing embodiment, the single cell-type fuel cell has been described. However, the invention can be applied to a lamination-type fuel cell, in which a plurality of cells is layered.

Furthermore, in the foregoing embodiment, as an electrochemical device using the cation conductor of the invention, descriptions have been given with reference to the fuel cell as an example. However, the cation conductor of the invention can be similarly applied to other electrochemical devices such as sensors, capacitors, and displays. Further, the cation conductor of the invention can be applied not only to the electrochemical devices utilizing protons, but also to electrochemical devices such as sensors, capacitors, and displays utilizing other cations of an element of Group 1 in the long-period periodic table such as lithium, sodium, potassium, and rubidium.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A mixture, comprising:
a first compound formed of 2-phenylimidazole; and
a second compound of at least one selected from the group consisting of a compound having a structure expressed in Chemical formula 1, a compound having a structure expressed in Chemical formula 2, and a compound having a structure expressed in Chemical formula 3:

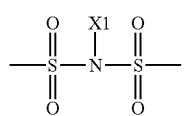

Chemical formula 1 where X1 represents an element of Group 1 in the long-period periodic table;

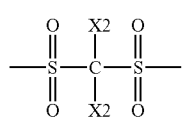

Chemical formula 2 where X2 represents an element of Group 1 in the long-period periodic table; and

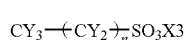

Chemical formula 3 where Y represents hydrogen or halogen, X3 represents an element of Group 1 in the long-period periodic table, and n represents a positive integer,
wherein the mixture is insoluble in water.

2. The mixture according to claim 1, wherein the second compound contains at least one of a polymer having the structure expressed in Chemical formula 1, and a polymer having the structure expressed in Chemical formula 2.

3. The mixture of claim 1, wherein the second compound is pentafluoroethanesulfonimide.

4. A cation conductor, comprising:
a first compound formed of 2-phenylimidazole; and
a second compound of at least one selected from the group consisting of a compound having a structure expressed in Chemical formula 4, a compound having a structure expressed in Chemical formula 5, and a compound having a structure expressed in Chemical formula 6:

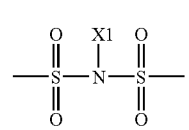

Chemical formula 4 where X1 represents an element of Group 1 in the long-period periodic table;

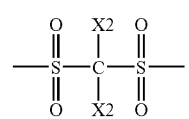

Chemical formula 5 where X2 represents an element of Group 1 in the long-period periodic table; and

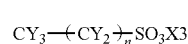

Chemical formula 6 where Y represents hydrogen or halogen, X3 represents an element of Group 1 in the long-period periodic table, and n represents a positive integer,
wherein a mixture of the first compound and the second compound is insoluble in water.

5. The cation conductor according to claim 4, wherein the second compound contains at least one of a polymer having the structure expressed in Chemical formula 4, and a polymer having the structure expressed in Chemical formula 5.

6. The cation conductor according to claim 4, further containing a support for supporting the first compound and the second compound.

7. The cation conductor according to claim 6, wherein the support contains a polymer.

8. The cation conductor according to claim 6, further containing a solvent.

9. The cation conductor of claim 4, wherein the second compound is pentafluoroethanesulfonimide.

10. An electrochemical device, comprising a pair of electrodes is arranged with a cation conductor in between,
wherein the cation conductor contains:
a first compound formed of 2-phenylimidazole; and
a second compound of at least one selected from the group consisting of a compound having a structure expressed in Chemical formula 7, a compound having a structure expressed in Chemical formula 8, and a compound having a structure expressed in Chemical formula 9:

Chemical formula 7

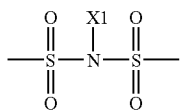

where X1 represents an element of Group 1 in the long-period periodic table; and Chemical formula 8

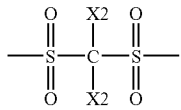

where X2 represents an element of Group 1 in the long-period periodic table;

Chemical formula 9

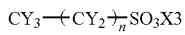

where Y represents hydrogen or halogen, X3 represents an element of Group 1 in the long-period periodic table, and n represents a positive integer wherein a mixture of the first compound and the second compound is insoluble in water.

11. The electrochemical device according to claim 10, wherein the second compound contains at least one of a polymer having the structure expressed in Chemical formula 7, and a polymer having the structure expressed in Chemical formula 8.

12. The electrochemical device according to claim 10, wherein the cation conductor further contains a support for supporting the first compound and the second compound.

13. The electrochemical device according to claim 12, wherein the support contains a polymer.

14. The electrochemical device according to claim 12, wherein the cation conductor further contains a solvent.

15. The electrochemical device according to claim 10, which is a fuel cell.

16. The electrochemical device of claim 10, wherein the second compound is pentafluoroethanesulfonimide.

* * * * *